US00PP32948P2

(12) United States Plant Patent
Rodriguez Mesa

(10) Patent No.: US PP32,948 P2
(45) Date of Patent: Apr. 6, 2021

(54) RASPBERRY PLANT NAMED 'EXPR02'

(50) Latin Name: ***Rubus idaeus* L.**
Varietal Denomination: EXPR02

(71) Applicant: Expoberries, S.A. de C.V., Los Reyes (MX)

(72) Inventor: Jose Maurilio Rodriguez Mesa, Los Reyes (MX)

(73) Assignee: Expoberries, S.A. de C.V., Los Reyes (MX)

( * ) Notice: Subject to any disclaimer, the term of this patent is extended or adjusted under 35 U.S.C. 154(b) by 0 days.

(21) Appl. No.: 16/602,485

(22) Filed: Oct. 17, 2019

(51) Int. Cl.
*A01H 5/08* (2018.01)
*A01H 6/74* (2018.01)

(52) U.S. Cl.
USPC ..... Plt./204

(58) Field of Classification Search
USPC ..... Plt./203, 204
See application file for complete search history.

*Primary Examiner* — Susan McCormick Ewoldt
(74) *Attorney, Agent, or Firm* — Jimmy Zhou

(57) ABSTRACT

The present invention is a new and distinct autumn primocane raspberry variety designated 'EXPR02'. This new variety was discovered after planting a seed produced by a controlled cross of 'SP821' (unpatented) and 'SP804' (unpatented). The new variety exhibits good productivity of red colored, conical shaped, firm fruit and sparse spine density.

6 Drawing Sheets

Latin name of the genus and species: *Rubus idaeus* L.
Variety denomination: 'EXPR02'.

BACKGROUND OF THE NEW VARIETY

The present invention relates to a new and distinct cultivar of raspberry hereinafter referred to as 'EXPR02'. The new and distinct variety of raspberry was developed from a hand pollination cross between the female parent raspberry plant 'SP804' and the male parent raspberry plant 'SP821'. This cross was made in Los Reyes, Michoacán, México in 2013.

The seed resulting from this controlled hybridization were germinated in a greenhouse in the autumn of 2013 and planted in a field in Los Reyes, Michoacán, Mexico. The seedlings fruited during the Autumn of 2014 and one, designated EXPR02 was selected for its excellent fruit quality, vigorous and productive plant, erect plant growth habit and tolerant to pest and disease.

During 2014, the original plant selection was propagated asexually from root cuttings in Los Reyes, Michoacán, Mexico and a test planting of one tunnel was established. A larger test planting was subsequently established in Zacoalco de Torres, Jalisco, México. The new variety has been asexually multiplied annually since 2014 by use of root cuttings and by tissue culture. During all asexual multiplication, the characteristics of the original plant have been maintained and no aberrant phenotypes have appeared.

SUMMARY OF THE NEW VARIETY

The present invention relates to a new and distinct raspberry variety. The varietal denomination of the new variety is 'EXPR02'. The new variety produces and maintains a strong vigorous plant with consistent fruit production from October through December on primocanes and in the ensuing year from the end of April through the beginning of June. Among the characteristics which distinguish the new variety from other varieties are a combination of characteristics which include the good productivity of red colored, conical shaped, firm fruit and sparse spine density.

BRIEF DESCRIPTION OF THE PHOTOGRAPHS

The accompanying photographs show typical characteristics of the new variety. The plants depicted in the photographs were grown in Zacoalco de Tones, Jalisco, Mexico.

DETAILED BOTANICAL DESCRIPTION

Figure 1:
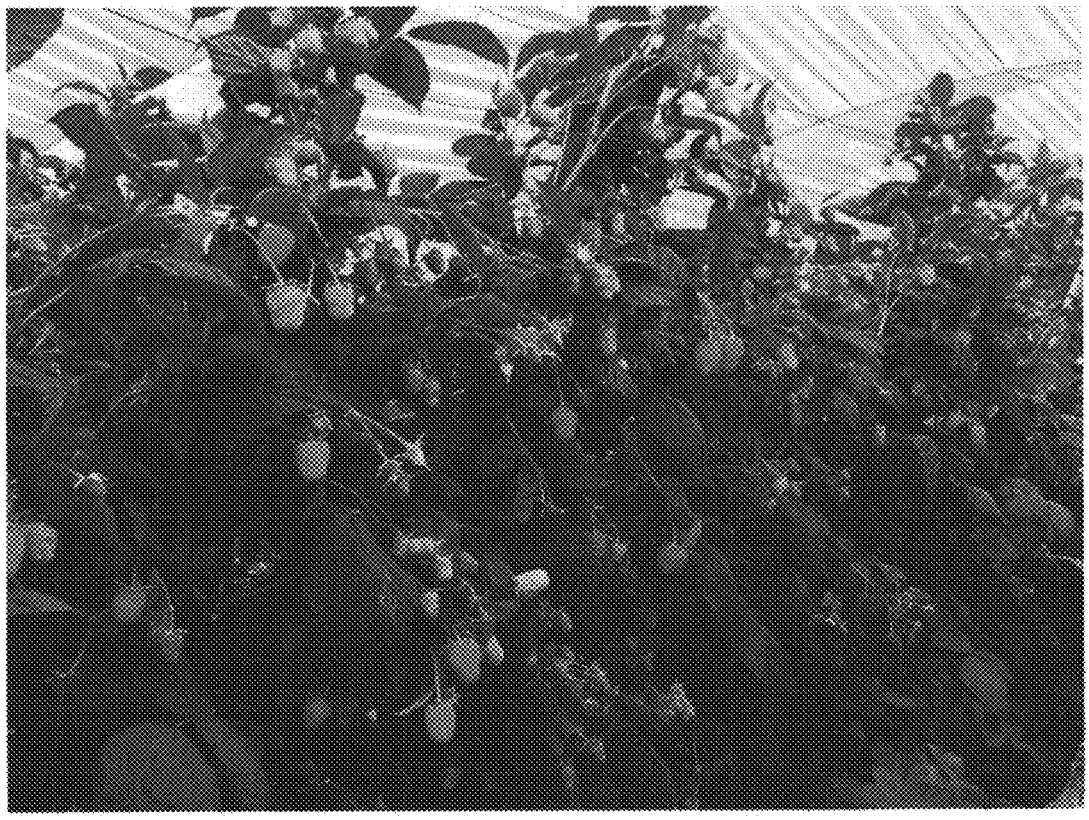
FIG. 1 shows several plants of the new variety exhibiting an upright habit with several red colored fruits.
Figure 2:
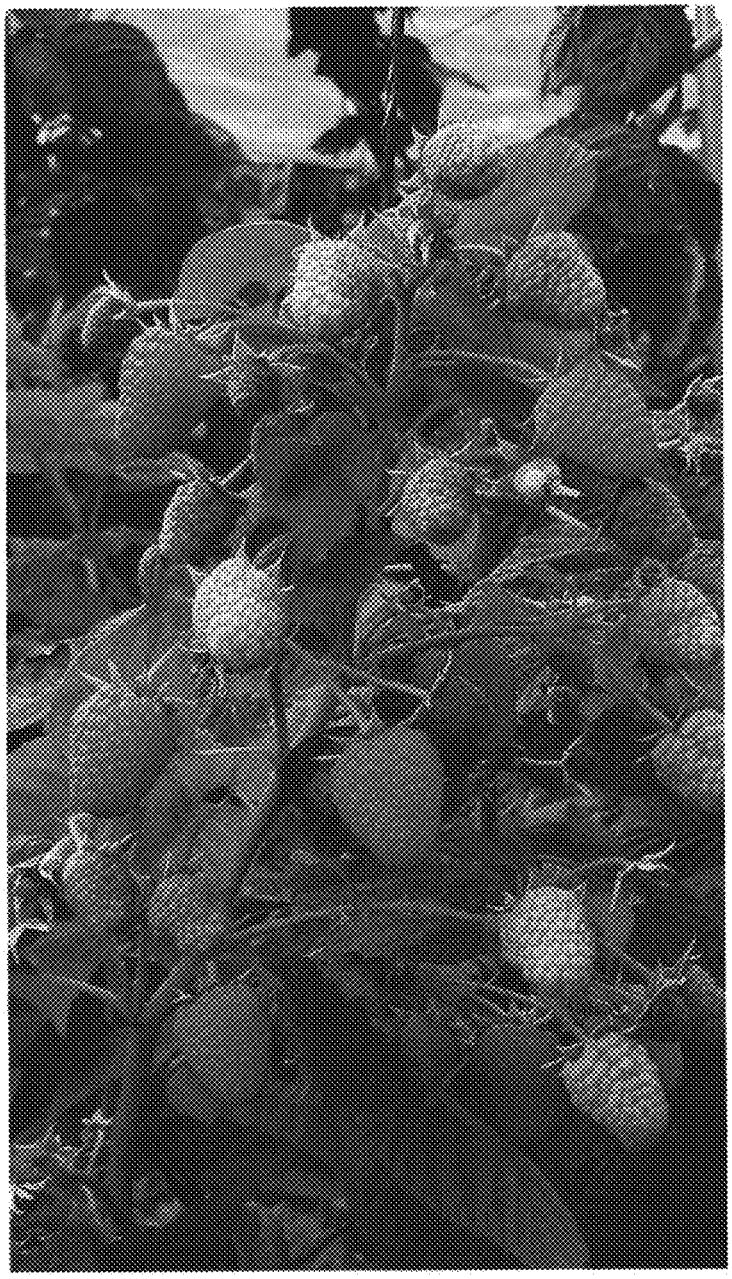
FIG. 2 shows a close-up view of several plants of the new variety with an upright habit with several red colored fruits.
Figure 3:
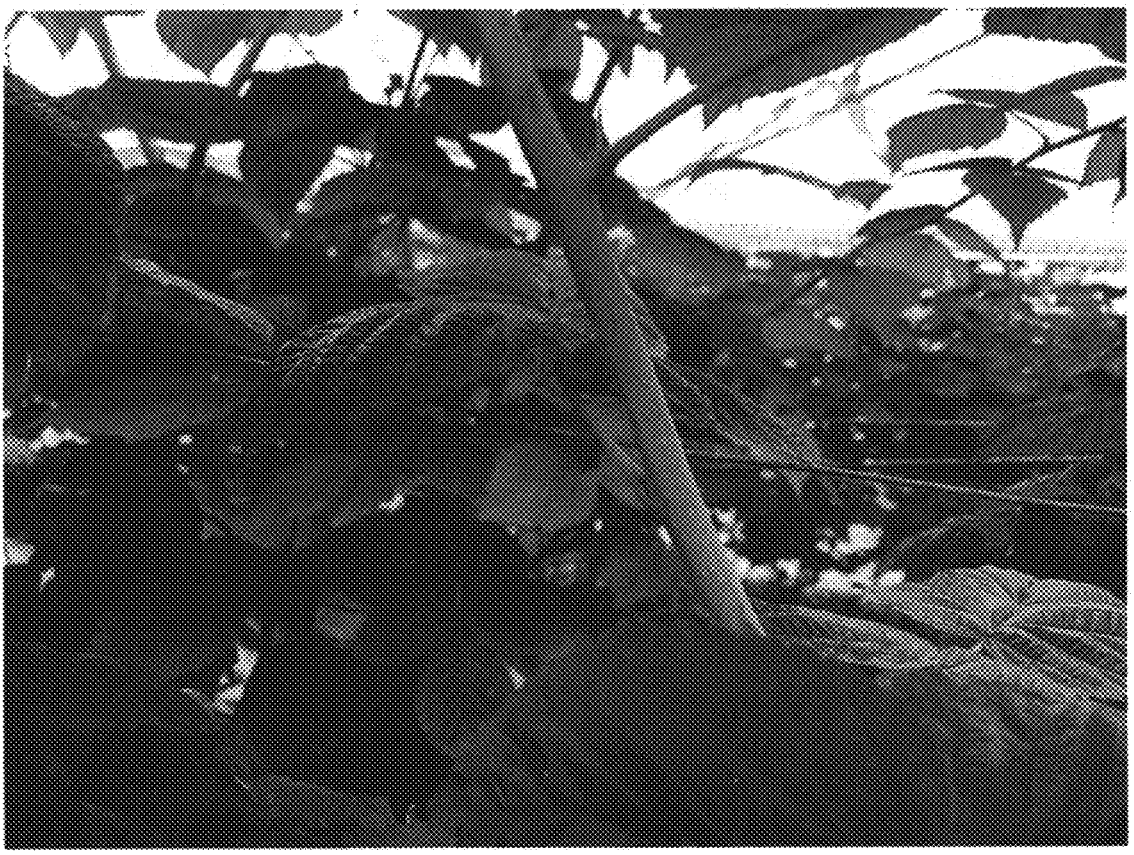
FIG. 3 shows the cane color of the new variety as RHS Strong Yellow Green (near 145 A) as well as the sparse spine density.
Figure 4:
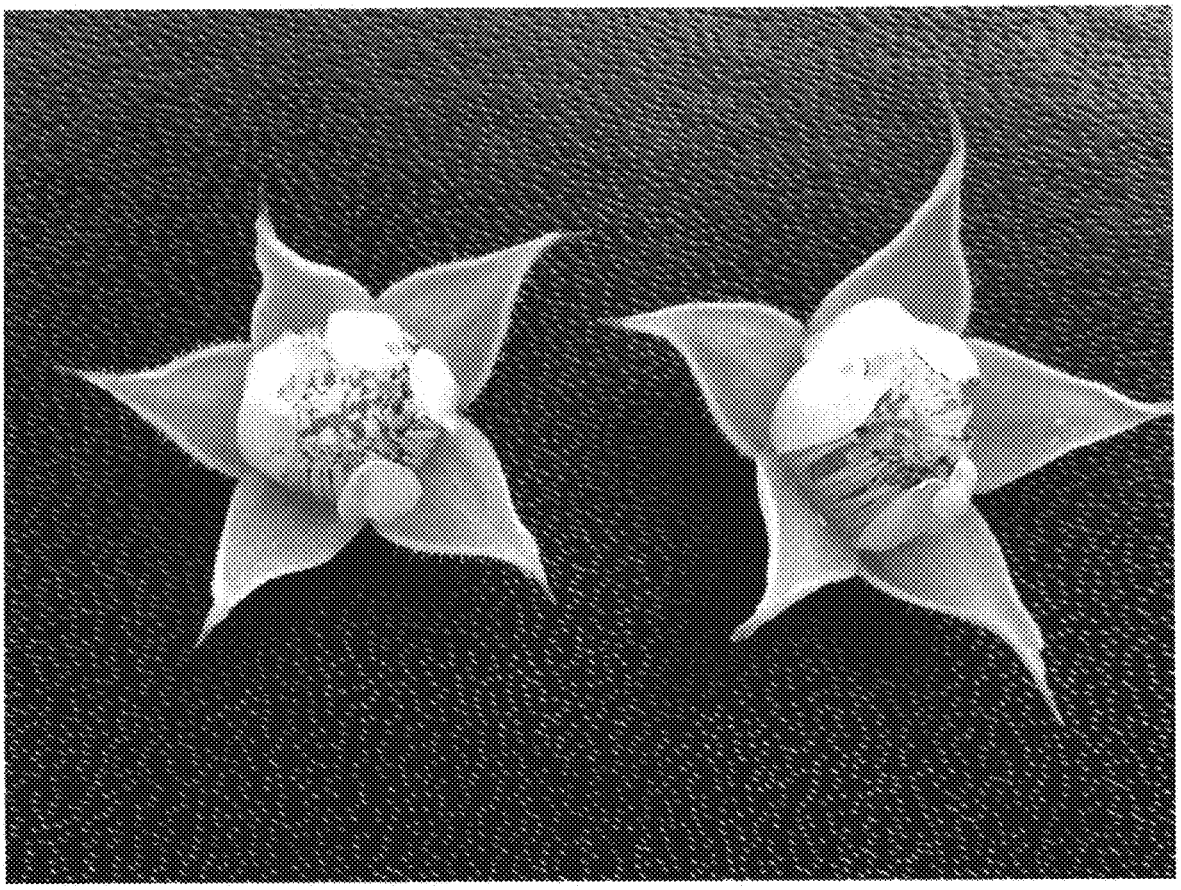
FIG. 4 shows typical flowers of the new variety having triangular shaped sepals with an acuminate apex and RHS Green group color (near 141 C to 141 D).
Figure 5:
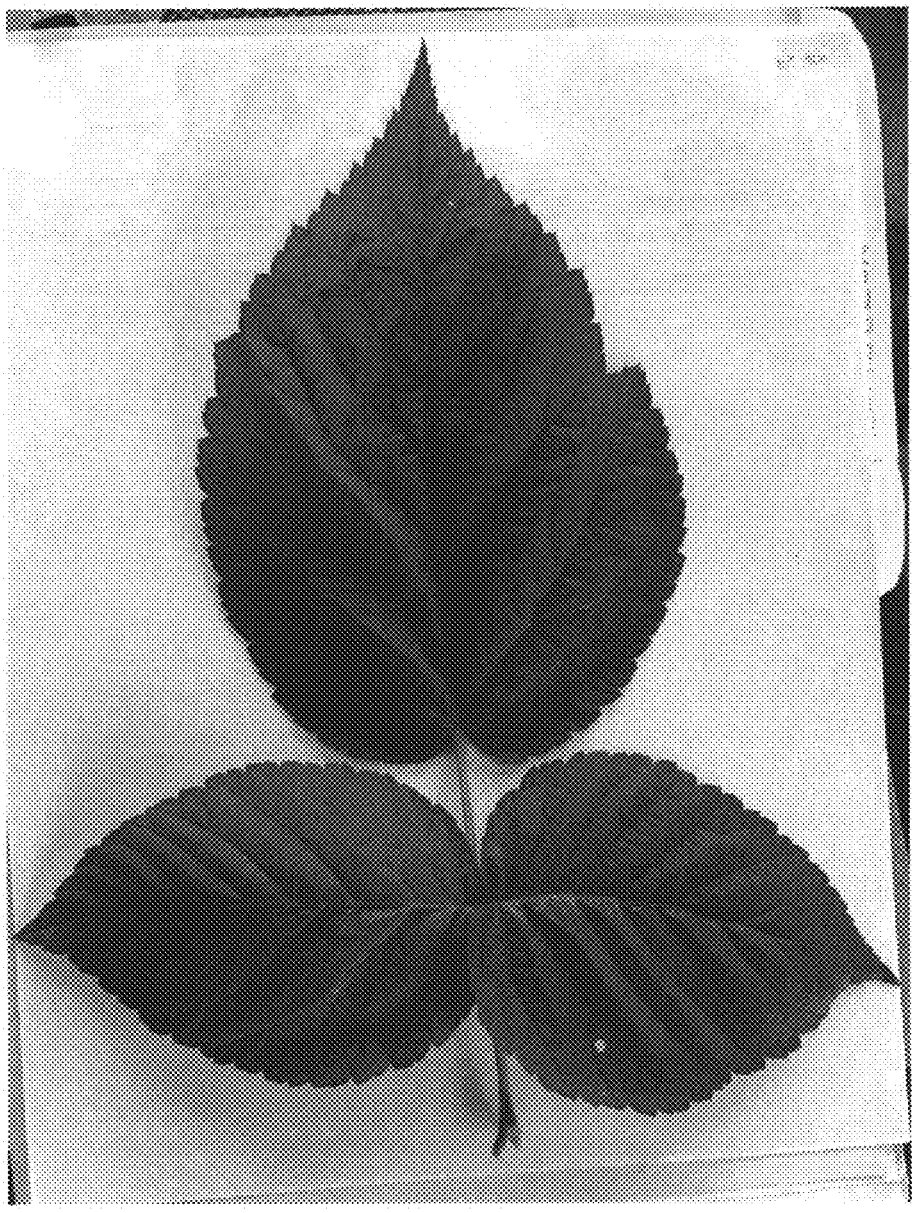
FIG. 5 shows the upper surface of a complete leaf of the new variety with RHS Moderate Olive Green color (near 137 A to 137 B)
Figure 6:
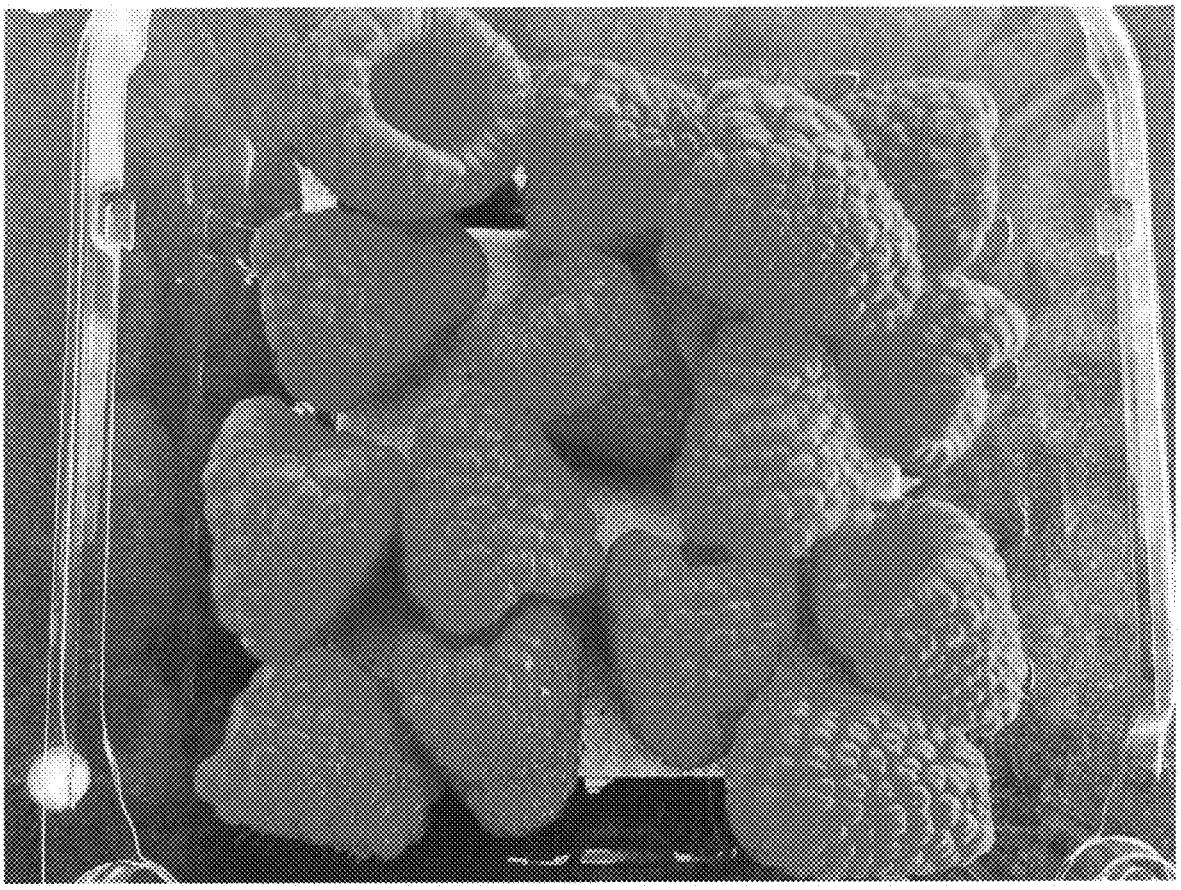
FIG. 6 shows typical fruits of the new variety having a conical shape, medium glossiness and RHS Red group color (between 43D to 43B).

The following is a detailed description of the new cultivar, including fruit production, together with the cultivar's morphological characteristics. The description is based upon observations taken of the fruits and plants grown at nursery Rancho El Briseno in the municipality of Zacoalco de Torres, Jalisco, Mexico. While root cutting is preferred, other known methods of propagating raspberry plants may be used.

The plants were grown in Zacoalco de Torres, Mexico in a 9 feet tall grow tunnel open at both ends. The average day temperature during the period of observation was 34° C. The average night temperature over the same period was 6° C.

Time from seed to first buttons averages 90 days. Pinch date is in autumn. The new variety has tested negative for Raspberry bushy dwarf idaeovirus, twospotted spider mite (*Tetranychus urticae* Koch), yellow rust (*Phragmidium rubi-idaei*) and phytopathogen fungi. The new variety is characterized by very short spines and sparse spine density. The red conical fruit is large and firm.

The new variety is closest to the 'Autumn Bliss' variety (U.S. Plant Pat. No. 6,597) but the new variety is distinguishable. For example, the new variety has larger fruit and a more upright habit than that of 'Autumn Bliss'. The fruit of 'Autumn Bliss' also exhibits a stronger coloration.

Plants and fruit of this new variety also differ phenotypically from its male parent 'SP821' (unpatented). The new variety is earlier ripening and possess better fruit firmness, better fruit flavor, better shelf life and more tolerant to pest and disease than 'SP821'. Unless indicated otherwise, color references are made to R.H.S. Colour Chart of The Royal Horticultural Society of London, 6th edition, 2015. The cane color in 'SP821' is yellow green (RHS yellow green group near 144 D to 144 C) whereas the cane color in the new variety is a strong yellow green (RHS 145 A). The spine of 'SP821' is brownish purple whereas the spines in the new variety has a strong yellow green color (RHS 145 A). In addition, the leaves in the new variety are smaller than the leaves in 'SP821'.

The new variety also differs phenotypically from its female parent 'SP804' (unpatented). The new variety is more vigorous than 'SP804'. The leaf of 'SP804' is light green whereas the leaf of the new variety is moderate olive green (138 C to 138 D). The spines in the new variety are strong yellow green, whereas 'SP804' are brownish purple. On the current season, flowering and fruit ripening begin early for the new variety, whereas flowering and fruit ripening begin late for 'SP804'. The shape of the new variety's fruit in lateral view is conical, whereas in 'SP804' the general shape in lateral view is conical.

The new variety is further characterized by high production yield. The plants used for the following information were two years old. The plants were grown in raised beds under tunnel. Water and fertilizer were applied through drip irrigation.

The characteristics of the new cultivar have been found to be stable and have been transmitted without change through succeeding asexual propagations. This propagation and testing has confirmed that the traits disclosed herein which characterize the new variety are fixed and retained true to type through successive generations.

The following description is in accordance with UPOV terminology and the color terminology herein is in accordance with The R.H.S. Colour Chart of The Royal Horticultural Society of London. The color descriptions and other phenotypical descriptions may deviate from the stated values and descriptions depending upon variation in environmental, seasonal and climatic conditions. Where dimensions, sizes, colors, and other characteristics are given, it is to be understood that such characteristics are approximations of averages set forth as accurately as practicable.

Classification:

*Family*.—Rosaceae.
*Botanical taxon*.—*Rubus idaeus* L.
*Common name*.—Raspberry.
*Variety name*.—'EXPR02'.

Plant:

*Habit*.—Upright.
*Vigor*.—Medium to strong.
*Length* (*free growth*).—About 210 cm.
*Length* (*commercial hedge*).—About 180 cm.
*Width* (*free growth*).—About 70 cm.
*Width* (*commercial hedge*).—About 70 cm.

Cultivar's primocane cane:

*Length*.—About 160 cm to 190 cm.
*Internode length*.—About 5 to 8 cm.
*Pubescence*.—Absent.
*Anthocyanin coloration of apex during rapid grow period*.—Absent.
*Cane color*.—RHS strong yellow green, near 145A.

Spines:

*Shape*.—Conical.
*Density*.—Sparse.
*Number/cm*.—About 0 to 3.
*Length*.—Very short.
*Width*.—About 0.1 cm at the base.
*Apex*.—Straight.
*Color*.—RHS strong yellow green, near 145A.

Leaf:

*Type*.—Compound.
*Number of leaflets*.—3.
*Arrangement of lateral leaflets*.—Free.
*Overlapping of lateral leaflets with terminal leaflet*.—Touching on the base.
*Upperside color*.—RHS moderate olive green, near 137A to 137B.
*Underside color*.—RHS green group color, near 138C to 138D.
*Length of entire complete leaf*.—About 25 cm.
*Width of entire complete leaf*.—About 22 cm.
*Profile of leaflets in cross section*.—Straight.
*Relief between veins*.—Medium.

Lateral leaflet:

*Shape*.—Ovate.
*Length*.—About 11.5 to 12 cm.
*Width*.—About 6.5 to 7.0 cm.
*Shape of tip*.—Acuminate.
*Shape of base*.—Round.
*Shape of margin*.—Serrate.
*Upperside rugosity*.—Medium to strong.
*Underside texture*.—Smooth.
*Upperside coloration*.—RHS green group color (near 137A-137B).
*Underside coloration*.—RHS green group color (near 138C to 138D).
*Venation pattern*.—Reticulate.
*Upperside venation coloration*.—RHS green group color (near 138A to 138B).
*Underside venation coloration*.—RHS green group color (near 138C to 138D).

Terminal leaflet:

*Length/width ratio*.—Longer than broad.
*Length*.—About 16.5 cm.
*Width*.—About 12.5 cm.
*Cross section*.—Straight.
*Upperside*.—RHS green group color (near 137A to 137B).
*Underside*.—RHS green group color (near 138C to 138D).
*Shape of leaflet*.—Palmate.
*Shape of tip*.—Acuminate.

*Shape of base*.—Round.
*Shape of margin*.—Double serrate.
*Upperside rugosity*.—Medium.
*Underside texture*.—Medium.
*Venation pattern*.—Reticulate or penniveined.
*Upperside venation coloration*.—RHS green group color (near 138A to 138B).
*Underside venation coloration*.—RHS green group color (near 138C to 138D).

Rachis:
*Length between the terminal leaflet and adjacent lateral leaflet*.—About 3.5 to 4.0 cm.
*Coloration*.—RHS green group color (near 138A to 138B).

Petiole:
*Color*.—RHS green group color (near 139B to 139C).
*Length*.—About 5.0 to 7.5 cm.
*Length* (*rachis with petiolule*).—About 9.0 to 11.0 cm.
*Spines*.—Very few and short.
*Diameter*.—About 2.5 to 3.5 mm in the petiolule and about 2.0 to 3.0 mm in the rachis.
*Texture*.—Smooth.

Stipule:
*Quantity per leaf*.—2.
*Shape*.—Spinose.
*Length*.—About 0.8 to 1.0 cm.
*Width*.—Very narrow, about 0.01 to 0.02 cm.
*Color* (*both surfaces*).—RHS yellow green group (near 144B to 144C).

Flower:
*Diameter*.—About 2.5 to 3.0 cm.
*Pedicel color*.—RHS yellow green group (near 144A to 144B).
*Depth*.—About 6.0 to 8.0 mm.

Flower bud:
*Shape*.—Trapezoidal.
*Diameter*.—About 0.7 to 0.9 cm.
*Length*.—About 1.0 to 1.2 cm.
*Color*.—RHS yellow green group (near 144A to 144B).

Pedicel:
*Length*.—About 2.5 to 3.0 cm.
*Diameter*.—About 2.0 to 3.0 mm.
*Surface texture*.—Smooth.
*Density of spines*.—Low.

Petal:
*Number of petals per flower*.—About 5 to 6.
*Shape*.—Narrow elliptique.
*Length*.—About 0.7 to 0.9 cm.
*Width*.—About 0.3 to 0.4 cm.
*Apex shape*.—Flat rounded.
*Base shape*.—Narrow.
*Margin*.—Smooth and regular.
*Texture*.—Smooth.
*Color* (*both surfaces*).—RHS white group color (near 155C to 155D).

Peduncles:
*Length*.—About 23.0 to 25.0 cm.
*Diameter*.—About 3.0 to 4.0 mm.
*Surface texture*.—Smooth.
*Density of spines*.—Medium.
*Color*.—RHS yellow green group (near 144C to 144D).

Receptacle:
*Length*.—About 2.2 to 2.8 cm.
*Diameter*.—About 1.0 to 1.2 cm.
*Shape*.—Conical.
*Color*.—RHS yellow green group (near 147D).

Sepal:
*Number of sepals per flower*.—About 5.
*Shape*.—Triangular.
*Length*.—About 0.8 to 1.0 cm.
*Width*.—About 0.4 to 0.5 cm.
*Apex shape*.—Acuminate.
*Base shape*.—Cupulate at the base forming the calyx.
*Margin*.—Smooth.
*Texture*.—Smooth.
*Color*.—RHS green group color (near 141C to 141D).

Reproductive organs:
*Number of pistils per flower*.—About 100 to 110.
*Pistil length*.—About 2 to 3 cm.
*Ovary shape*.—Pyriform.
*Ovary length*.—Short.
*Ovary width*.—Narrow.
*Ovary color*.—RHS green group color (near 142D to 142C).
*Style length*.—About 1.5-2.5 mm.
*Style color*.—RHS white group color (near 155C).
*Number of stamens per flower*.—About 90 to 100.
*Stamen length*.—About 4 to 5 mm.
*Stamen shape*.—Ovate.
*Stamen color*.—RHS white group color (near 155C).
*Pollen*.—Amount: Moderate to abundant.
*Pollen color*.—RHS yellow green group (near 153B to 153A).

Fruit:
*Shape*.—Conical.
*Length*.—About 2.6 to 2.8 cm.
*Width*.—About 1.8 to 2.4 cm.
*Color*.—RHS red group color (near 43C).
*Number of drupelets per fruit*.—About 90 to 110.
*Size of single drupelet*.—About 0.3 to 0.4 cm.
*Drupelet arrangement around the berry*.—Regular.
*Glossiness*.—Medium.
*Firmness*.—Firm.
*Adherence to plug*.—Medium.
*Diameter hollow center*.—About 2.2 to 2.8 cm.
*Average weight*.—6.0 g.
*Average productivity*.—3.6 pounds per plant.

Seeds:
*Number of seeds per drupelet*.—1.
*Shape*.—Reniform.
*Color*.—RHS greyed-orange group (near 174C to 174D).
*Surface texture*.—Wrinkled.

Fruit bearing type: Primocane.

Fruiting lateral cane (number of fruit per fruiting lateral cane): About 25 fruits.

The raspberries of 'EXPR02' are suitable for sale and human consumption as fresh fruit. The shelf life of the new variety is good. It is suitable for consumption for 4 weeks after pinching date at 2° C. to 4° C. At 1° C. to 2° C., it is suitable for sale and human consumption for up to 40 days. The fruit is also amenable to processing. While root cutting is preferred, other known methods of propagating raspberry plants may be used.

What is claimed:

1. A new and distinct raspberry plant known as 'EXPR02' as described herein, illustrated and identified by the characteristics set forth above.

* * * * *